(12) United States Patent
Kato

(10) Patent No.: US 6,552,001 B1
(45) Date of Patent: Apr. 22, 2003

(54) METHOD BREEDING AND FEEDS

(75) Inventor: Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/762,217

(22) PCT Filed: Aug. 3, 1999

(86) PCT No.: PCT/JP99/04162

§ 371 (c)(1),
(2), (4) Date: Feb. 5, 2000

(87) PCT Pub. No.: WO00/07586

PCT Pub. Date: Feb. 17, 2000

(30) Foreign Application Priority Data

Aug. 4, 1998 (JP) ............................................. 10-220444
Sep. 7, 1998 (JP) ............................................. 10-252443
Nov. 13, 1998 (JP) ............................................. 10-323457

(51) Int. Cl.$^7$ ............................................. A61K 31/70
(52) U.S. Cl. ............................................. 514/25
(58) Field of Search ............................................. 514/25

(56) References Cited

FOREIGN PATENT DOCUMENTS

| | | |
|---|---|---|
| EP | 0 941 981 | 9/1999 |
| EP | 0 974 347 A1 | 1/2000 |
| JP | 51 22582 | 2/1976 |

*Primary Examiner*—Zohreh Fay
(74) *Attorney, Agent, or Firm*—Browdy and Neimark, P.L.L.C.

(57) ABSTRACT

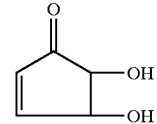

A method of rearing useful organisms such as cultured animals which is effective in preventing the organisms from diseases, treating the organisms for diseases or maintaining the health of the organisms, characterized by administering to the organisms (1) a product of heat treatment of at least one compound selected from the group consisting of (a) uronic acid and uronic acid derivatives, (b) sugar compounds containing uronic acid and/or uronic acid derivatives and (c) substances which contain sugar compounds containing uronic acid and/or uronic acid derivatives, (2) 4,5-dihydroxy-2-cyclopenten-1-one represented by formula (I), and/or (3) a 4,5-dihydroxy-2-cyclopenten-1-one derivative; and feeds effective therein.

16 Claims, No Drawings

US 6,552,001 B1

METHOD BREEDING AND FEEDS

The present application is the national stage under 35 U.S.C. 371 of PCT/JP99/04162, filed Aug. 3, 1999.

TECHNICAL FIELD

The present invention relates to a method for breeding an organism and a feed.

BACKGROUND ART

Recently, culture of useful organisms such as domestic animals, laboratory animals, domestic fowls, fishes and shrimps have remarkably become popular. On the other hand, occurrence of various diseases, underdevelopment and the like caused by stress due to a breeding environment such as packed breeding have become problems.

OBJECTS OF INVENTION

The main object of the present invention is to provide a method for breeding an organism and a feed useful for preventing or treating diseases of useful organisms such as cultured animals and for maintaining the health of the useful organisms.

SUMMARY OF INVENTION

The present invention is outlined as follows. The first invention of the present invention relates to a method for breeding an organism, characterized in that the method comprises administering:

(1) a heat treatment product of at least one compound selected from the group consisting of (a) uronic acid or a uronic acid derivative; (b) a saccharide containing uronic acid and/or a uronic acid derivative; and (c) a material containing a saccharide containing uronic acid and/or a uronic acid derivative;

(2) 4,5-dihydroxy-2-cyclopenten-1-one of formula (I):

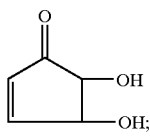

[1]

and/or (3) a derivative of 4,5-dihydroxy-2-cyclopenten-1-one of formula (I), to an organism.

The second invention of the present invention relates to a feed for an organism which contains, which is produced by adding thereto, and/or which is produced by diluting a heat treatment product of at least one compound selected from the group consisting of (a), (b) and (c) as described above; 4,5-dihydroxy-2-cyclopenten-1-one of formula (I); and/or a derivative of 4,5-dihydroxy-2-cyclopenten-1-one of formula (I).

The third invention of the present invention relates to a composition for breeding an organism which contains a heat treatment product of at least one compound selected from the group consisting of (a), (b) and (c) as described above; 4,5-dihydroxy-2-cyclopenten-1-one of formula (I); and/or a derivative of 4,5-dihydroxy-2-cyclopenten-1-one of formula (I).

In the first to third inventions of the present invention, the organism is, for example, a cultured animal or a pet animal.

The cultured organism is exemplified by a domestic animal, a laboratory animal, a domestic fowl, a fish, a crustacean and a shellfish. The heat treatment product is exemplified by a material containing 4,5-dihydroxy-2-cyclopenten-1-one of formula (I).

The feed of the second invention of the present invention is exemplified by a feed for improving physical condition.

The composition for breeding an organism of the third invention of the present invention is exemplified by a composition for soaking an organism, an additive for a feed, and an additive for a drink.

DETAILED DESCRIPTION OF THE INVENTION

As used herein, a heat treatment product of at least one compound selected from the group consisting of uronic acid or a uronic acid derivatives a saccharide containing uronic acid and/or a uronic acid derivative; and a material containing a saccharide containing uronic acid and/or a uronic acid derivative is not limited to a specific one as long as it has an effect of increasing efficiency of breeding an organism such as viability, fattening rate, spawning rate, birthrate or weaning rate.

Uronic acid is (also called as glycuronic acid) a generic name for hydroxyaldehyde-acids in which the aldehyde group of aldose is kept intact and only the primary alcohol group at the other end is oxidized into a carboxyl group. Uronic acid naturally exists as constituents of various polysaccharides in animals and plants.

Examples of uronic acids which can be used in the present invention include, but are not limited to, galacturonic acid, glucuronic acid, gluronic acid, mannuronic acid and iduronic acid. Derivatives of uronic acid include lactones, esters, amides and salts thereof.

As used herein, examples of saccharides containing uronic acid and/or a uronic acid derivative include, but are not limited to, pectin, pectic acid, alginic acid, hyaluronic acid, heparin, heparan sulfate, fucoidan, chondroitin sulfate, chondroitin and dermatan sulfate. Decomposition products (products of chemical, enzymatic or physical treatment) of the above-mentioned saccharides as well as derivatives and salts of the decomposition products can also be used.

As used herein, a material containing a saccharide containing uronic acid and/or a uronic acid derivative is not limited to a specific one as long as the material contains the above-mentioned saccharide containing uronic acid and/or a uronic acid derivative. Materials containing a saccharide containing uronic acid and/or a uronic acid derivative derived from plants, algae, microorganisms and animals can be used.

Alternatively, a processed agricultural or marine food product containing uronic acid and/or a uronic acid derivative may be used directly or after drying and grinding as a raw material for the heat treatment product in the present invention.

A method used for the heat treatment in the production of the heat treatment product of the present invention is not limited to a specific one as long as it produces a heat treatment product having physiological activities such as an activity of increasing breeding efficiency and an activity of improving physical condition. At least one compound selected from the group consisting of uronic acid or a uronic acid derivative; a saccharide containing uronic acid and/or a uronic acid derivative; and a material containing a saccharide containing uronic acid and/or a uronic acid derivative may be heated, for example, at 60–350° C. for a few seconds to a few days, preferably at 80–150° C. for a few minutes to a few days. A heat treatment product used in the present invention can be obtained by heating pectin or alginic acid, for example, at 80–150° C. for a few minutes to a few days. Furthermore, a heat treatment product of interest can be obtained by heating uronic acid, a lactone of uronic acid or a uronic acid ester at 60–150° C. for a few minutes to a few days.

Either wet heating or dry heating may be used for the heat treatment in the present invention. Among these, wet heating is preferable in view of production efficiency of a compound contained in the heat treatment product of the present invention having physiological activities such as an activity of increasing breeding efficiency and an activity of improving physical condition, for example, 4,5-dihydroxy-2-cyclopenten-1-one of formula (I) (hereinafter simply referred to as cyclopentenone). Any wet heating such as steam heating, pressurized steam heating and pressurized heating can be used. Direct heating using dry hot wind and indirect heating through a division wall from a heat source can be used as dry heating. Direct heating is exemplified by air current dry heating and spray dry heating. Drum dry heating and the like can be used as indirect heating.

Any methods may be used for producing cyclopentenone of the present invention. Cyclopentenone may be synthesized according to a chemical synthesis method [Carbohydrate Res., 247:217–222 (1993); Helvetica Chimica Acta, 55:2838–2844 (1972)]. Cyclopentenone produced in a heat treatment product of at least one compound selected from the group consisting of uronic acid or a uronic acid derivative; a saccharide containing uronic acid and/or a uronic acid derivative; and a material containing a saccharide containing uronic acid and/or a uronic acid derivative, or a product purified therefrom can be used. These heat treatment products containing cyclopentenone as well as products partially purified or purified therefrom can be used in the present invention (WO 98/13328).

A method used for the heat treatment in the production of the heat treatment product containing cyclopentenone of the present invention is not limited to a specific one as long as it produces cyclopentenone. Uronic acid or a uronic acid derivative; a saccharide containing uronic acid and/or a uronic acid derivative; or a material containing a saccharide containing uronic acid and/or a uronic acid derivative may be heated, for example, at 60–350° C. for a few seconds to a few days, preferably at 80–150° C. for a few minutes to a few days. A heat treatment product containing cyclopentenone can be obtained by heating pectin or alginic acid, for example, at 80–150° C. for a few minutes to a few days. Furthermore, a heat treatment product containing cyclopentenone of interest can be obtained by heating uronic acid, a lactone of uronic acid or a uronic acid ester at 60–150° C. for a few minutes to a few days.

Although the pH used for the heat treatment is not limited to a specific one, it is preferable to carry out the heat treatment under neutral to acidic conditions. The pH for the heat treatment may be adjusted depending on the raw material used. The production of cyclopentenone is usually accelerated by heating under acidic conditions.

The concentration of the raw material during the heat treatment is within any range in which cyclopentenone can be produced by heat treatment. The concentration may be determined in consideration of operationality, yield and the like.

Either wet heating or dry heating may be used for the heat treatment in the present invention. Among these, wet heating is preferable in view of production efficiency of cyclopentenone. Any wet heating such as steam heating, pressurized steam heating and pressurized heating can be used. Direct heating using dry hot wind and indirect heating through a division wall from a heat source can be used as dry heating. Direct heating is exemplified by air current dry heating and spray dry heating. Drum dry heating and the like can be used as indirect heating.

Cyclopentenone in the heat treatment product used in the present invention may be collected by known purification/isolation means including chemical means and physical means. Conventional purification means such as gel filtration, fractionation using a molecular weight fractionating membrane, solvent extraction, fractional distillation and various chromatographies (ion-exchange resins, normal phase or reverse phase) can be used in combination to collect cyclopentenone produced in the heat treatment product.

For example, cyclopentenone is produced in a heat treatment product by heating a 1% solution of D-glucuronic acid as uronic acid at 121° C. for 4 hours. Cyclopentenone in the heat treatment product is extracted with a solvent. The extract is concentrated. The concentrate is then separated on silica gel column chromatography. Eluted fractions containing cyclopentenone are concentrated. Cyclopentenone is extracted from the concentrate with chloroform, thereby isolating cyclopentenone in the heat treatment product.

Furthermore, cyclopentenone is purified by subjecting the heat treatment product of glucuronic acid to an ion-exchange resin column, preferably an anion-exchange resin column and collecting non-adsorptive fractions. Alternatively, purified cyclopentenone can be obtained by the following steps. The heat treatment product of glucuronic acid is subjected to an activated carbon column. Non-adsorptive fractions are removed. The column is washed. Elution is carried out using a hydrophilic organic solvent (e.g., an aqueous ethanol solution, preferably an aqueous ethanol solution at a concentration of 40% or more). In addition, highly purified cyclopentenone can be obtained by combining these methods.

A derivative of 4,5-dihydroxy-2-cyclopenten-1-one (hereinafter simply referred to as a cyclopentenone derivative) can also be used in the present invention. The cyclopentenone derivative is not limited to a specific one as long as the objects of the present invention can be accomplished by using the derivative. Cyclopentenone derivatives of formulas (II) to (V) are exemplified:

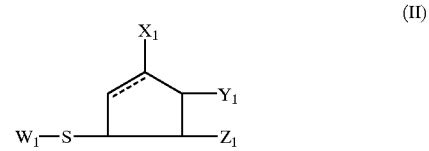

(II)

wherein the bond in the five-membered ring represented by a broken line means that the five-membered ring may be either a cyclopentene ring having a double bond or a saturated cyclopentane ring; if the five-membered ring is a cyclopentene ring, $X_1$ is OH, $Y_1$ is $=$O and $Z_1$ is H; if the five-membered ring is a cyclopentane ring, $X_1$ is $=$O, $Y_1$ is OH and $Z_1$ is OH; $W_1$ is a residue in which an SH group is removed from an SH group-containing compound;

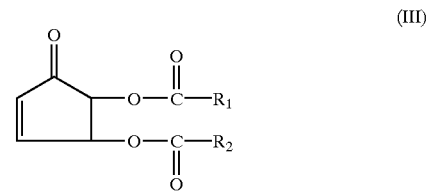

(III)

wherein $R_1$ and $R_2$ may be identical or different each other, and are hydrogen, an aliphatic group, an aromatic group or an aromatic aliphatic group;

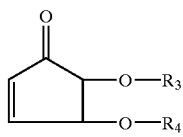

wherein $R_3$ and $R_4$ may be identical or different each other, and are hydrogen, an aliphatic group, an aromatic group or an aromatic aliphatic group, provided that $R_3$ and $R_4$ are not simultaneously H; and

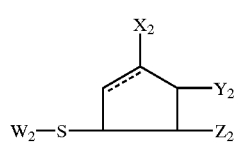

wherein the bond in the five-membered ring represented by a broken line means that the five-membered ring may be either a cyclopentene ring having a double bond or a saturated cyclopentane ring; if the five-membered ring is a cyclopentene ring, $X_2$ is $OR_5$, $Y_2$ is $=O$ and $Z_2$ is H; if the five-membered ring is a cyclopentane ring, $X_2$ is $=O$, $Y_2$ is $OR_6$ and $Z_2$ is $OR_7$; $R_5$ is $R_8$ or $-(CO)-R_9$; $R_6$ is H, $R_{10}$ or $-(CO)-R_{11}$; $R_8$ is H, $R_{12}$ or $-(CO)-R_{13}$ ($R_8$, $R_9$, $R_{10}$, $R_{11}$, $R_{12}$ and $R_{13}$ may be identical or different each other, and are an aliphatic group, an aromatic group or an aromatic aliphatic group; $R_9$, $R_{11}$ and $R_{13}$ may be H), provided $R_6$ and $R_7$ are not simultaneously H; $W_2$ is a residue in which an SH group is removed from an SH group-containing compound.

Optical isomers of the materials containing the cyclopentenone derivatives or salts thereof can be used in the present invention.

The cyclopentenone derivative of formula (II) is described in detail in WO 98/39291. The derivative can be obtained by reacting cyclopentenone with an SH group-containing compound such as cysteine or glutathione. A material containing the cyclopentenone derivative can be obtained by adding an SH group-containing compound to a material containing cyclopentenone. The derivatives are exemplified by compounds of formulas (VI) to (IX):

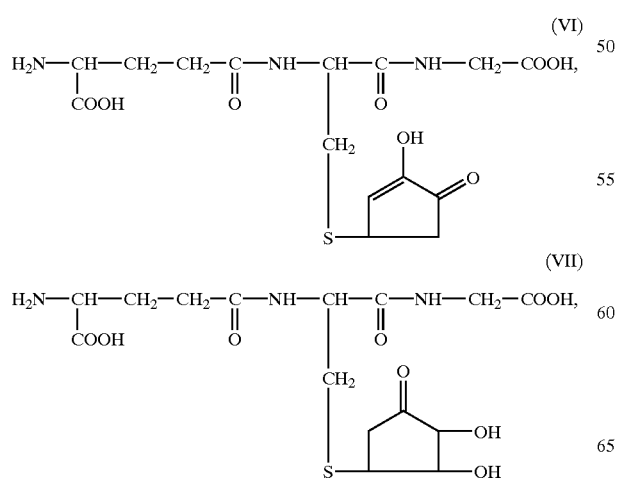

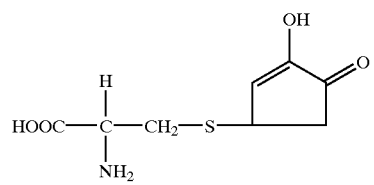

and

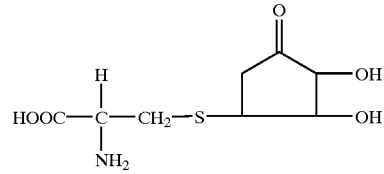

The compound of formula (VI) is a product of reaction between cyclopentenone and glutathione under acidic conditions. The compound of formula (VII) is a product of reaction between cyclopentenone and glutathione under neutral conditions. The compound of formula (VIII) is a product of reaction between cyclopentenone and cysteine under acidic conditions. The compound of formula (IX) is a product of reaction between cyclopentenone and cysteine under neutral conditions.

The cyclopentenone derivative of formula (III) is described in detail in WO 98/40346 and Japanese Patent Application No. 10-231659. The derivative can be obtained by simultaneously or sequentially reacting cyclopentenone with a carboxylic acid having an aliphatic group, an aromatic group or an aromatic aliphatic group and/or a reactive derivative thereof. The cyclopentenone derivative is exemplified by diacetylcyclopentenone, dibenzoylcyclopentenone, dihexanoylcyclopentenone, dimyristoylcyclopentenone, dioctanoylcyclopentenone, di-3-octenoylcyclopentenone, dibutyrylcyclopentenone, didecanoylcyclopentenone, divalerylcyclopentenone, dipropionylcyclopentenone, di-2-hexenoylcyclopentenone, diisobutyrylcyclopentenone, dimethoxyacetylcyclopentenone, methoxyfumarylcyclopentenone and methoxymaleylcyclopentenone. Formula (X) below represents the structure of dipropionylcyclopentenone. Formula (XI) below represents the structure of dibenzoylcyclopentenone.

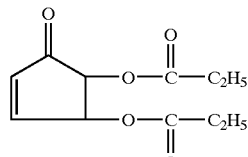

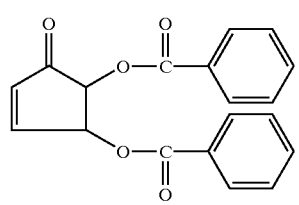

The cyclopentenone derivative of formula (IV) is described in detail in WO 99/00349. The derivative can be obtained by simultaneously or sequentially reacting cyclopentenone with an alcohol having an aliphatic group, an aromatic group or an aromatic aliphatic group and/or a reactive derivative thereof. The cyclopentenone derivative is exemplified by 4-benzylcyclopentenone ether, 5-benzylcyclopentenone ether, 4,5-dibenzylcyclopentenone ether, 4-t-butylcyclopentenone ether, 5-t-butylcyclopentenone ether and 4,5-di-t-butylcyclopentenone ether. Formulas (XII) and (XIII) below represent the structures of 5-benzylcyclopentenone ether and 4,5-di-t-butylcyclopentenone ether, respectively.

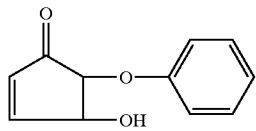
(XII)

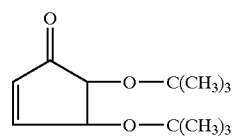
(XIII)

The cyclopentenone derivative of formula (V) is described in detail in Japanese Patent Application No. 10-232746. The derivative can be obtained by reacting the compound of formula (III) or the compound of formula (IV) with an SH group-containing compound such as cysteine or glutathione. Examples of the derivatives include compounds of formulas (XIV) and (XV) below.

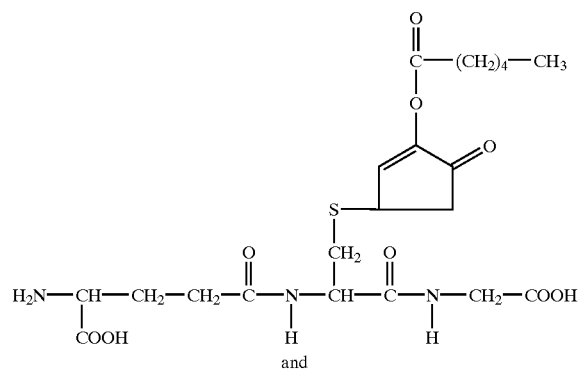
(XIV)

and

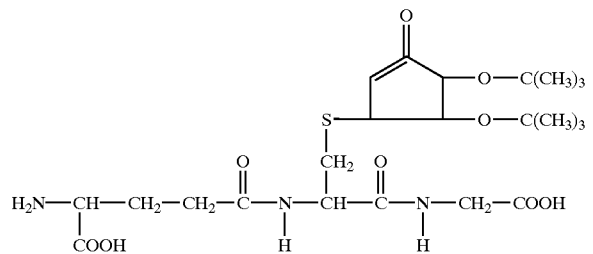
(XV)

The compound of formula (XIV) is a product of reaction between dihexanoylcyclopentenone and glutathione. The compound of formula (XV) is a product of reaction between 4,5-di-t-butylcyclopentenone ether and glutathione.

A cyclopentenone derivative having an α,β unsaturated carbonyl structure can be preferably used in the present invention.

The heat treatment product, cyclopentenone or a cyclopentenone derivative used in the present invention has physiological activities such as a carcinostatic activity, an antiproliferation activity against tumor cells, an apoptosis-inducing activity, an activity of inhibiting topoisomerase II, an activity of inducing differentiation in tumor cells, an antirheumatic activity, an activity of inhibiting rheumatoid arthritis, an activity of inducing Fas antigen production, an antimicrobial activity, an antiviral activity, an activity of improving liver function, an activity of inducing heat shock protein, an activity of normalizing blood component, an activity of enhancing tumor immunity, an anti-inflammatory activity, an activity of inhibiting tumor necrosis factor production, an activity of inhibiting nitrogen monoxide production and immunoregulatory activities such as an activity of inhibiting delayed hypersensitivity, an activity of inhibiting lymphocyte blastogenesis, an activity of inhibiting mixed lymphocyte reaction, an activity of inhibiting IgE production and an activity of inhibiting carrageenan edema. Based on these activities, the feed of the present invention which contains the heat treatment product, cyclopentenone and/or a cyclopentenone derivative used in the present invention as an active ingredient is very useful as a feed for improving physical condition of an organism such as a feed for activating biological defense mechanism, a feed for activating antibody production mechanism, a feed for normalizing saccharide metabolism or a feed effective in protecting and preventing infection with pathological organism.

The cyclopentenone compound of formula (II) produced from cyclopentenone and an SH group-containing compound is produced as a metabolite in an organism in the presence of cyclopentenone and an SH group-containing compound. The feeds of the present invention include a feed that contains cyclopentenone and an SH group-containing compound such as cysteine or glutathione and in which the cyclopentenone derivative is produced in the feed or in a living body. Such a feed is very effective as the feed of the present invention.

The daily dosage of the heat treatment product of at least one compound selected from the group consisting of uronic acid or a uronic acid derivative; a saccharide containing uronic acid and/or a uronic acid derivative; and a material containing a saccharide containing uronic acid and/or a uronic acid derivative (hereinafter simply referred to as the heat treatment product of the present invention) is usually 1 to 20000 mg per kg body weight of the organism of interest. The heat treatment product can be added to and mixed with raw materials for an artificial mixed feed. Alternatively, it can be mixed with powder raw materials for an artificial mixed feed, and then added to and mixed with other raw materials.

A daily dosage of cyclopentenone and/or a derivative thereof is usually 0.01 to 200 mg per kg body weight of the organism of interest (e.g., a cultured animal). It can be added to and mixed with raw materials for an artificial mixed feed. Alternatively, it can be mixed with raw materials of powder form for an artificial mixed feed, and then added to and mixed with other raw materials. At least one compound selected from the group consisting of cyclopentenone, a derivative thereof and the heat treatment product of the present invention can be directly added to and mixed with a feed for the organism of interest.

The content of the heat treatment product of the preset invention in the feed for the organism of interest is not limited to a specific one and may be determined depending on the objects. The suitable content is 0.05 to 50 w/w %.

The content of cyclopentenone and/or a derivative thereof in the feed for the organism of interest is not limited to a specific one and may be determined depending on the objects. The suitable content is 0.001 to 1 w/w %.

Artificial mixed feeds include those produced using raw materials derived from animal such as fish powder, casein and squid meal, raw materials derived from plant such as soybean cake, wheat flour, starch and feed yeast, animal oil such as cod-liver oil and squid-liver oil, vegetable oil such as soybean oil and rape-seed oil, vitamins, minerals, amino acids, antioxidants and the like as raw materials. The artificial mixed feeds also include feeds for fishes such as minced fish meat.

The method for producing the feed of the present invention is not limited to a specific one as long as the produced feed contains, is produced by adding thereto and/or is produced by diluting at least one compound selected from the group consisting of cyclopentenone, a derivative thereof and the heat treatment product of the present invention.

At least one compound selected from the group consisting of cyclopentenone, a derivative thereof and the heat treatment product of the present invention can be administered to an organism of interest by directly adding the compound to water or seawater in a pool, a water tank, a reservoir tank or a breeding area and soaking the organism therein. This soaking method is particularly effective when the intake of feed by an organism of interest is reduced.

The concentration of cyclopentenone and/or a derivative thereof in water or seawater is not limited to a specific one and may be determined depending on the objects. The suitable concentration is 0.00001 to 0.01 w/w %.

The concentration of the heat treatment product of the present invention in water or seawater is not limited to a specific one and may be determined depending on the objects. The suitable concentration is 0.005 to 5 w/w %.

Furthermore, a drink containing at least one compound selected from the group consisting of cyclopentenone, a derivative thereof and the heat treatment product of the present invention may be given to an organism of interest as a drink for breeding.

The concentration of cyclopentenone and/or a derivative thereof in a drink is not limited to a specific one and may be determined depending on the objects. The suitable concentration is 0.0001 to 1 w/w %.

The concentration of the heat treatment product of the present invention in a drink is not limited to a specific one and may be determined depending on the objects. The suitable concentration is 0.005 to 5 w/w %.

A composition for breeding an organism containing at least one compound selected from the group consisting of cyclopentenone, a derivative thereof and the heat treatment product of the present invention as an active ingredient (e.g., a composition for soaking an organism, an additive for a feed and an additive for a drink) may be produced according to conventional methods.

Organisms to which the present invention can be applied include, but are not limited to, cultured animals such as domestic animals (e.g., horses, cows, pigs, sheep, goats, camels and llamas), laboratory animals (e.g., mice, rats, guinea pigs and rabbits), domestic fowls (e.g., chickens, ducks, turkeys and ostriches), fishes (e.g., red sea breams, parrot fishes, bastard halibuts, flatfishes, yellowtails, young yellowtails, amberjacks, tunas, yellow jacks, sweetfishes, salmon, trout, tiger globefishes, eels, lochs and catfishes), crustaceans (e.g., prawns, black tiger shrimps, yellow sea prawns and blue crabs) and shellfishes (e.g., abalones, turban shells, scallops and oysters) as well as pet animals (e.g., dogs and cats). The present invention can be widely applied to land animals and aquatic animals.

No death was observed when cyclopentenone or a derivative thereof was orally administered to a mouse at a single dosage of 100 mg/kg. Furthermore, no death was observed when the heat treatment product of the present invention was orally administered to a mouse at a single dosage of 300 mg/kg.

Bacterial infection and viral infection in an organism of interest such as a domestic animal, a laboratory animal, a domestic fowl, a fish, a crustacean, a shellfish or a pet animal is prevented or treated. Such prevention or treatment can be accomplished by giving a feed containing at least one compound selected from the group consisting of cyclopentenone, a derivative thereof and the heat treatment product of the present invention to the organism. Alternatively, the prevention or the treatment can be accomplished by soaking the organism in a solution containing at least one compound selected from the group consisting of cyclopentenone, a derivative thereof and the heat treatment product of the present invention. Furthermore, disease states in an infected organism is remarkably ameliorated. Additionally, the health of an organism of interest is maintained, resulting in remarkable improvement in viability, fattening rate, spawning rate, birthrate, weaning rate, growth rate or the like.

Cultured animals had the following problems. (1) Diseases due to bacterial infection frequently occur. Since the organisms are cultured in a limited area, all of them will be infected and die in a short period of time once an infectious disease occurs. (2) The organisms are susceptible to parasite infections, nutritional diseases, environmental diseases and tumors. (3) Great stress due to the narrow breeding area causes the cultured organisms to rub the body surface to the breeding facilities and be scratched. The scratches make bacteria and parasites easy to adhere to the animals. (4) Intake of feed decreases due to the stress, resulting in retarded growth. The feed for improving physical condition of the present invention can greatly decrease the stress in the cultured animal bred in a narrow area, prevent the rubbing of the body surface to breeding facilities, make the appetite of the organism better, and remarkably increase growth rate, birthrate, spawning rate, weaning rate, disease prevention rate and the like based on its various physiological activities such as an antimicrobial activity, an anti-inflammatory activity and an antioxidant activity.

The present invention provides a feed for a land animal or an aquatic animal and a solution for soaking an organism containing at least one compound selected from the group consisting of cyclopentenone, a derivative thereof and the heat treatment product of the present invention. The feed and the solution are very useful as an antibacterial feed, an antiviral feed, an antibacterial solution for soaking an organism and an antiviral solution for soaking an organism.

The present invention provides a method for breeding a land animal or an aquatic animal, and a method for treating or preventing a disease in a land animal or an aquatic animal such as an infectious disease caused by a pathological microorganism such as a bacterium, a fungus or a virus, characterized in that the method comprises administering at least one compound selected from the group consisting of cyclopentenone, a derivative thereof and the heat treatment product of the present invention to the animal.

Furthermore, the present invention provides a method for breeding an organism, or treating or preventing a disease, characterized in that the method comprises soaking a land animal or an aquatic animal in an aqueous solution containing at least one compound selected from the group consisting of cyclopentenone, a derivative thereof and the heat treatment product of the present invention.

The method of the present invention is remarkably effective in treating or preventing infections diseases in cultured fishes (e.g., infection of bastard halibuts with lymphocystis virus, infection with gliding bacteria, and white-mouth disease, an infectious disease in globefishes). When onset or sign of these infectious diseases are recognized, loss of commercial value or occurrence of damage due to these diseases can be prevented by using the feed of the present invention or the method for soaking an organism of the present invention. Furthermore, conventionally used antibiotics and formalin are not required according to the present invention. Thus, problems associated with the residual toxicity thereof are solved.

EXAMPLES

The following examples further illustrate the present invention in detail but are not to be construed to limit the scope thereof.

Referential Example 1

(1) Pomosin Pectin Type LM-13CG (Hercules) or Alginic Acid HFD (Dainippon Pharmaceutical) was suspended in water at a concentration of 1%. The suspensions were heated at 121° C. for 4 hours to prepare heat treatment products. The respective heat treatment products were lyophilized to prepare a heat treatment product of pectin (containing 2% cyclopentenone) and a heat treatment product of alginic acid (containing 1.8% cyclopentenone).

(2) Alginic Acid HFD, non-swelling alginic acid (Wako Pure Chemical Industries, code 011-13341), dried powder of Kjellmaniella crassifolia, dried powder of Ascophyllum nodosum (product name: Algin Gold, sold by Andes Boeki) or dried powder of Lessonia nigrescence (product name: Seaweed Powder: sold by Andes Boeki) was suspended in water at a concentration of 5%. After adjusting the pH to about 2 using HCl, the suspensions were heated at 121° C. for 4 hours. Solids were removed from the respective heated mixtures by centrifugation and heated supernatants were obtained.

The respective heated supernatants were analyzed on HPLC to determine the yields of cyclopentenone. The conditions used for HPLC were as follows. TSK gel DOS-80TSQA (4.6×250 mm); flow rate: 1 ml/min., elution: water+0.1% TFA (0–15 min.) and 50% acetonitrile+0.1% TFA (15–30 min.); detection: UV 215 nm. HPLC analysis was carried out under the same conditions using cyclopentenone at a given concentration to prepare a calibration curve based on the area. The cyclopentenone concentration in each sample was then determined.

As a result, 10.9 mM, 9.63 mM, 1.89 mM, 1.87 mM and 1.75 mM of cyclopentenone was produced in the heated supernatants of Alginic Acid HFD, alginic acid, dried powder of tangle, dried powder of Ascophyllum nodosum and dried powder of Lessonia nigrescence, respectively. These supernatants were used as cyclopentenone-containing solutions.

(3) 10 g of D-glucuronic acid (Sigma, G 5269) was dissolved in 1 liter of water. The solution was heated at 121° C. for 4 hours and then concentrated to a volume of about 10 ml under reduced pressure. 40 ml of an upper layer of a mixture of butyl acetate:acetic acid:water=3:2:2 was added thereto and mixed. A supernatant obtained by centrifuging the mixture was concentrated under reduced pressure to a volume of about 10 ml.

The extract was applied to silica gel BW-300SP for column chromatography (2×28 cm, Fuji Sylysia). Separation was carried out using an upper layer of butyl acetate:acetic acid:water=3:2:2 as an eluent, at a pressure of 0.2 kg/cm$^2$ using a compressor and at a flow rate of 5 ml/min. Each fraction contained 10 ml of the fractionated eluate. A portion of each fraction was analyzed on thin-layer chromatography. As a result, 61st to 80th fractions contained cyclopentenone with high purity. These fractions were collected and concentrated under reduced pressure. The concentrate was extracted with 40 ml of chloroform. The extract was concentrated under reduced pressure to obtain 100 mg of cyclopentenone.

The preparation was separated on normal phase HPLC using Palpack Type S column and detected on the basis of ultraviolet absorbance at 215 nm. This procedure confirmed that the preparation had a purity of 98%.

Example 1

The heat treatment product of alginic acid as described in Referential Example 1-(1) was added at a concentration of 2.2 g/l to a water tank (containing 2000 l of seawater) containing 1300 young bastard halibuts (average body weight: 350 g) suffered from lymphocystis disease during culturing on land. The diseased bastard halibuts were soaked in the solution of the heat treatment product for 30 minutes. 7000 l of seawater was then added to the tank. The diseased bastard halibuts were soaked for additional 30 minutes. After soaking, 5000 l of seawater was further added thereto. Then, the water was replaced with seawater.

A feed for diseased bastard halibuts was prepared by adding 7 kg of the heat treatment product of alginic acid to 134 kg of the moist feed as shown in Table 1 below. The feed was given to the soaked bastard halibuts twice a day such that the heat treatment product of alginic acid was given at 0.78 g/kg/day.

TABLE 1

| Horse mackerel | 45 kg |
| Oonago (sand lance) | 48 kg |
| Nutrient "Kairyoku" (Bayer) | 750 kg |
| Mixed feed mash for culturing (Kirin Beer) | 40 kg |

White mass around the mouth in the bastard halibuts disappeared 24 days after the initiation of administration of feed. The lymphocystis disease states were ameliorated in most bastard halibuts. 500 out of the 1300 bastard halibuts were cured, and 665 out of 1300 were getting better at day 24, indicating the remarkable effect of the heat treatment product. No relapse of lymphocystis disease was observed.

As described above, effects of curing a disease in fishes and ameliorating disease states were observed when fishes were soaked in the solution of the heat treatment product of the present invention and the feed was given to the fishes.

Similar effects were also observed using the heat treatment product as described in Referential Example 1-(2), cyclopentenone as described in Referential Example 1-(3) or a cyclopentenone derivative.

Furthermore, no occurrence of lymphocystis disease was observed when the solution of the heat treatment product of the present invention, the heat treatment product as described in Referential Example 1-(2), cyclopentenone or a cyclopentenone derivative was used for fishes without lymphocystis disease, indicating the remarkable preventive effect of them.

Example 2

A feed for young bastard halibuts (average body weight: 350 g) suffered from lymphocystis disease during culturing in sea was prepared by adding 3 kg of the heat treatment product of alginic acid as described in Referential Example 1-(1) to 136 kg of the moist feed as shown in Table 2 below. The feed was given to the fishes once in two days such that the heat treatment product of alginic acid was given at 1.2 g/kg/feeding.

TABLE 2

| "Hamachi Moist FVNE" (Nisshin Flour Milling) | 60 kg |
|---|---|
| Horse mackerel | 75 kg |
| Nutrient "SD Mix No. 1" (Takeda Food) | 1 kg |

Mass around the mouth in 600 out of the 1800 diseased bastard halibuts disappeared after eighth feeding. Thus, these fishes were cured of lymphocystis disease, and they could be transferred to another fish preserve. 900 out of the 1800 bastard halibuts were almost cured, whereas 300 out of the 1800 bastard halibuts died. 600 new bastard halibuts with lymphocystis disease joined with the 900 fishes that were getting better. Feeds were administered to the fishes four more times. 400 out of the 1500 fishes were cured and amelioration of disease states was observed in 800 out of 1500. No relapse of lymphocystis disease or occurrence of another disease was observed, indicating the preventive effect of the heat treatment product.

As described above, oral administration of the heat treatment product of the present invention was effective against a disease in fishes. About eight feedings were required for exerting the effect.

Similar effects were also observed using the heat treatment product as described in Referential Example 1-(2), cyclopentenone as described in Referential Example 1-(3) or a cyclopentenone derivative. Furthermore, no occurrence of infection was observed when fishes without infection were similarly treated, indicating their effect of preventing infections in fishes.

Example 3

Young bastard halibuts with gliding bacteria disease (body weight: about 4 g) cultured on land were divided into four groups. Effect of the heat treatment product of alginic acid as described in Referential Example 1-(1) on gliding bacteria disease was examined.

Control group: 2400 young bastard halibuts were fed with commercially available dry pellets (Otohime No. 4: Nisshin Flour Milling) once a day. They were bred in a 25000-l seawater tank.

Soaked group: A water tank for soaking was prepared by adding 880 g of the heat treatment product of alginic acid to 400 l of seawater and starting oxygen supply. 2375 young bastard halibuts were distributed in baskets such that several hundreds of the fishes were contained in a basket. They were soaked in the water tank for soaking for 30 minutes. After soaking, they were bred in a 25000-l seawater tank being fed with commercially available dry pellets once a day.

Group administered with the heat treatment product of alginic acid (1): 2380 young bastard halibuts were bred in a 25000-l seawater tank being fed once a day with a feed prepared by adding 500 g of the heat treatment product of alginic acid to 78 kg of a moist feed as shown in Table 3 below.

Group administered with the heat treatment product of alginic acid (2): 2357 young bastard halibuts were bred in a 25000-l seawater tank being fed once a day with a feed prepared by adding 5200 g of the heat treatment product of alginic acid to 88 kg of a moist feed as shown in Table 4 below.

The results are shown in Table 5.

TABLE 3

| Krill | 12 kg |
|---|---|
| Sand lance | 12 kg |
| Squid | 12 kg |
| Hamachi Moist Eight (Nisshin Flour Milling) | 40 kg |
| Aqua Base 2 (Nisshin Flour Milling) | 2 kg |

TABLE 4

| Krill | 12 kg |
|---|---|
| Sand lance | 12 kg |
| Squid | 12 kg |
| Hamachi Moist Eight (Nisshin Flour Milling) | 50 kg |
| Aqua Base 2 (Nisshin Flour Milling) | 2 kg |

TABLE 5

| | Number of dead fishes |
|---|---|
| Control group | 286 |
| Soaked group | 57 |
| Group administered with the heat treatment product of alginic acid (1) | 66 |
| Group administered with the heat treatment product of alginic acid (2) | 21 |

As shown in Table 5, the numbers of dead fishes in the soaked group, the administration group (1) and the administration group (2) were decreased as compared with those in the control group at the ninth day of the examination, indicating the effect of the heat treatment product of alginic acid on gliding bacteria disease.

Similar effects were also observed using the heat treatment product as described in Referential Example 1-(2), cyclopentenone as described in Referential Example 1-(3) or a cyclopentenone derivative. Furthermore, no occurrence of infection was observed when fishes without infection were similarly treated, indicating their effect of preventing infections in fishes.

Example 4

A feed containing the heat treatment product of alginic acid to be given a day to 2000 tiger globefishes (average body weight: 450 g) suffered from white-mouth disease during culturing in sea was prepared upon use as follows. 1.11 kg of the heat treatment product of alginic acid as described in Referential Example 1-(1) was dissolved in water to a volume of 1.5 l. 10 kg of dry pellet feed (Otohime for globefish: Nisshin Flour Milling) was soaked with the solution. The entire feed was given to the fishes once a day such that 20 mg/kg body weight/day of cyclopentenone was given (group administered with the feed containing the heat treatment product of alginic acid).

As a control, 10 kg of the dry pellet feed (otohime for globefish: Nisshin Flour Milling) was given to 2000 tiger globefishes with white-mouth disease (average body weight: 450 g) once a day (control group)

The feed containing the heat treatment product of alginic acid was given for 3 weeks. 202 out of the 2000 tiger globefishes with white-mouth disease died in the control group. On the other hand, 121 out of the diseased 2000 tiger globefishes died in the group administered with the feed containing the heat treatment product of alginic acid, resulting in reduction of mortality by about half. In particular, 53 fishes died in the control group whereas only 8 fishes died in the group administered with the feed containing the heat treatment product of alginic acid during the third week. These results demonstrated that administration of the heat treatment product of alginic acid for 3 weeks was sufficient for treating white-mouth disease. No relapse of white-mouth disease was observed in the cured tiger globefishes, indicating the effect of preventing infections with white-mouth disease.

As described above, oral administration of the heat treatment product of the present invention was remarkably effective against an infectious disease in globefishes. Similar effects were also observed using the heat treatment product as described in Referential Example 1-(2), cyclopentenone as described in Referential Example 1-(3) or a cyclopentenone derivative. Furthermore, no occurrence of infection was observed when fishes without infection were similarly treated, indicating their effect of preventing infections in fishes.

Example 5

100 g of the heat treatment product of pectin as described in Referential Example 1-(1) was added to 60 kg of moist pellets. The mixture was given to 3 years old sea breams every other day, resulting in increase in the ratio of spawning and spawning rate. Similar effects were also observed using the heat treatment product of alginic acid as described in Referential Example 1-(1), the heat treatment product as described in Referential Example 1-(2), cyclopentenone as described in Referential Example 1-(3) or a cyclopentenone derivative.

Furthermore, no occurrence of infection was observed in fishes administered with the above, indicating the effect of preventing infections.

Example 6

The heat treatment product of pectin as described in Referential Example 1-(1) was given to 8 weeks old female chickens in a commercially available mixed feed at 12 mg/kg/day, resulting in increase in spawning rate.

Similar effects were observed when cyclopentenone as described in Referential Example 1-(3) was given to 8 weeks old female chickens in a commercially available mixed feed at 63 pg/kg/day.

Similar effects were also observed using the heat treatment product of alginic acid as described in Referential Example 1-(1), the heat treatment product as described in Referential Example 1-(2) or a cyclopentenone derivative.

Furthermore, no occurrence of infection was observed in chickens administered with the above, indicating the effect of preventing infections in birds.

What is claimed is:

1. A method for breeding an organism, characterized in that the method comprises administering:
   (1) a heat treatment product of at least one compound selected from the group consisting of (a) uronic acid or a uronic acid derivative; (b) a saccharide containing uronic acid and/or a uronic acid derivative; and (c) a material containing a saccharide containing uronic acid and/or a uronic acid derivative;
   (2) 4,5-dihydroxy-2-cyclopenten-1-one of formula (I):

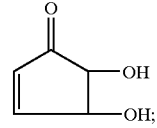

[1]

and/or
   (3) a derivative of 4,5-dihydroxy-2-cyclopenten-1-one of formula (I), to an organism.

2. The method according to claim 1, wherein the organism is a cultured animal or a pet animal.

3. The method according to claim 2, wherein the cultured organism is a domestic animal, a laboratory animal, a domestic fowl, a fish, a crustacean or a shellfish.

4. The method according to claim 1, wherein the heat treatment product is a material containing 4,5-dihydroxy-2-cyclopenten-1-one of formula (I).

5. A feed for an organism which is produced by adding thereto, and/or which is produced by diluting, comprising:
   (1) a heat treatment product of at least one compound selected from the group consisting of (a) uronic acid or a uronic acid derivative; (b) a saccharide containing uronic acid and/or a uronic acid derivative; and (c) a material containing a saccharide containing uronic acid and/or a uronic acid derivative;
   (2) 4,5-dihydroxy-2-cyclopenten-1-one of formula (I):

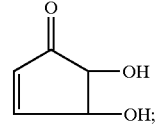

[1]

and/or
   (3) a derivative of 4,5-dihydroxy-2-cyclopenten-1-one of formula (I).

6. The feed according to claim 5, which is a feed for a cultured animal or a feed for a pet animal.

7. The feed according to claim 6, wherein the cultured organism is a domestic animal, a laboratory animal, a domestic fowl, a fish, a crustacean or a shellfish.

8. The feed according to claim 5, which is a feed for improving physical condition.

9. The feed according to claim 5, wherein the heat treatment product is a material comprising 4,5-dihydroxy-2-cyclopenten-1-one of formula (I).

10. A composition for breeding an organism which contains:
    (1) a heat treatment product of at least one compound selected from the group consisting of (a) uronic acid or a uronic acid derivative; (b) a saccharide containing uronic acid and/or a uronic acid derivative; and (c) a material containing a saccharide containing uronic acid and/or a uronic acid derivative;

(2) 4,5-dihydroxy-2-cyclopenten-1-one of formula (I):

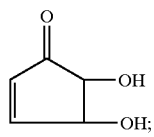

and/or (3) a derivative of 4,5-dihydroxy-2-cyclopenten-1-one of formula (I).

11. The composition according to claim 10, which is a composition for breeding a cultured animal or a composition for breeding a pet animal.

12. The composition according to claim 11, wherein the cultured organism is a domestic animal, a laboratory animal, a domestic fowl, a fish, a crustacean or a shellfish.

13. The composition according to claim 10, wherein the heat treatment product is a material comprising 4,5-dihydroxy-2-cyclopenten-1-one of formula (I).

14. The composition according to claim 10, which is a composition for soaking an organism.

15. The composition according to claim 10, which is an additive for a feed.

16. The composition according to claim 10, which is an additive for a drink.

\* \* \* \* \*

UNITED STATES PATENT AND TRADEMARK OFFICE
CERTIFICATE OF CORRECTION

PATENT NO. : 6,552,001 B1
DATED : April 22, 2003
INVENTOR(S) : Kato

It is certified that error appears in the above-identified patent and that said Letters Patent is hereby corrected as shown below:

<u>Title page,</u>
Item [86], "(2) (4)", delete "Feb. 5, 2000" and insert therefor -- Feb. 5, 2001 --.

Signed and Sealed this

Twenty-sixth Day of August, 2003

JAMES E. ROGAN
*Director of the United States Patent and Trademark Office*